United States Patent
Boas

(10) Patent No.: US 8,233,586 B1
(45) Date of Patent: Jul. 31, 2012

(54) ITERATIVE REDUCTION OF ARTIFACTS IN COMPUTED TOMOGRAPHY IMAGES USING FORWARD PROJECTION AND AN EDGE-PRESERVING BLUR FILTER

(75) Inventor: Franz Edward Boas, Palo Alto, CA (US)

(73) Assignee: Franz Edward Boas, Burlingame, CA (US)

( * ) Notice: Subject to any disclaimer, the term of this patent is extended or adjusted under 35 U.S.C. 154(b) by 0 days.

(21) Appl. No.: 13/030,088

(22) Filed: Feb. 17, 2011

(51) Int. Cl.
*A61B 6/00* (2006.01)

(52) U.S. Cl. ............... 378/4; 378/57; 378/207; 382/131

(58) Field of Classification Search ............... 378/4, 57, 378/207
See application file for complete search history.

(56) References Cited

U.S. PATENT DOCUMENTS

| | | | | |
|---|---|---|---|---|
| 5,243,664 | A * | 9/1993 | Tuy | 382/130 |
| 5,907,594 | A | 5/1999 | Lai | |
| 5,933,471 | A | 8/1999 | Kalvin | |
| 6,094,467 | A * | 7/2000 | Gayer et al. | 378/4 |
| 6,507,633 | B1 * | 1/2003 | Elbakri et al. | 378/8 |
| 7,023,951 | B2 * | 4/2006 | Man | 378/8 |
| 7,187,794 | B2 * | 3/2007 | Liang et al. | 382/131 |
| 7,254,209 | B2 * | 8/2007 | Zhao et al. | 378/4 |
| 7,340,027 | B2 * | 3/2008 | Timmer | 378/4 |
| 7,636,461 | B2 | 12/2009 | Spies et al. | |
| 7,991,243 | B2 * | 8/2011 | Bal et al. | 382/275 |
| 2005/0123215 | A1 * | 6/2005 | Man | 382/275 |
| 2008/0273651 | A1 * | 11/2008 | Boas | 378/4 |

OTHER PUBLICATIONS

G. Glover, et al, "An algorithm for the reduction of metal clip artifacts in CT reconstructions," Medical Physics, vol. 8, pp. 799-807, Nov.-Dec. 1981.
W. Kalender, et al, "Reduction of CT artifacts caused by metallic implants," Radiology, vol. 164, pp. 576-577, Aug. 1987.
A.C. Kak and M. Slaney, Principles of computerized tomographic imaging, IEEE Press, New York, 1988.
D. Verhoeven, "Limited-data computed tomography algorithms for the physical sciences," Applied optics, vol. 32, No. 20, pp. 3736-3754, Jul. 10, 1993.
B. De Man, et al, "Reduction of metal streak artifacts in x-ray computed tomography using a transmission maximum a posteriori algorithm," IEEE transactions on nuclear science, vol. 47, No. 3, pp. 977-981, Jun. 2000.
S. Vandenberghe, et al, "Iterative reconstruction algorithms in nuclear medicine," Computerized medical imaging and graphics, vol. 25, pp. 105-111, 2001.
D. Prell, et al, "A novel forward projection-based metal artifact reduction method for flat-detector computed tomography," Phys Med Biol, vol. 54, pp. 6575-6591, Nov. 2009.

* cited by examiner

*Primary Examiner* — Alexander H Taningco

(57) ABSTRACT

We present an iterative method for reducing artifacts in computed tomography (CT) images. First, a filter is applied to the experimental projection data that adaptively expands the detector element size in regions with low photon counts, until the desired number of photons are detected. The initial image is then calculated using an existing reconstruction technique. In each iteration, artifacts and noise in the current image are reduced by using an edge-preserving blur filter. Metal pixels (determined from the initial image) are replaced with smaller values. The resulting image is forward projected. Rays that go through metal are replaced with the forward projected values. Rays that do not pass near metal are kept at the experimental values. Filtered backprojection is then performed on the new projection data to determine the updated image. Finally, after the last iteration, metal pixels are copied from the initial image.

9 Claims, 4 Drawing Sheets

| Method | Average image quality rank | Example 1 (embolization coils) | Example 2 (bilateral hip replacements) |
|---|---|---|---|
| MDT (present invention) | 1.0 |  |  —8 |
| LI | 2.1 |  |  —9 |
| FBP | 3.5 |  |  —10 |
| SART | 3.5 |  |  —11 |

ITERATIVE REDUCTION OF ARTIFACTS IN COMPUTED TOMOGRAPHY IMAGES USING FORWARD PROJECTION AND AN EDGE-PRESERVING BLUR FILTER

REFERENCES CITED

U.S. Patent Documents

| | | | |
|---|---|---|---|
| 5,907,594 | May 1999 | Lai | 378/4 |
| 5,933,471 | August 1999 | Kalvin | 378/4 |
| 7,023,951 B2 | April 2006 | Man | 378/8 |
| 7,636,461 B2 | December 2009 | Spies | 382/128 |
| 2008/0273651 | November 2008 | Boas | 378/4 |

Other Publications

G. Glover, et al, "An algorithm for the reduction of metal clip artifacts in CT reconstructions," *Medical Physics*, vol. 8, pp. 799-807, November-December 1981.

W. Kalender, et al, "Reduction of CT artifacts caused by metallic implants," *Radiology*, vol. 164, pp. 576-77, August 1987.

A. C. Kak and M. Slaney, *Principles of computerized tomographic imaging*, IEEE Press, New York, 1988.

D. Verhoeven, "Limited-data computed tomography algorithms for the physical sciences," *Applied optics*, vol. 32, no. 20, pp. 3736-54, Jul. 10, 1993.

B. De Man, et al, "Reduction of metal streak artifacts in x-ray computed tomography using a transmission maximum a posteriori algorithm," *IEEE transactions on nuclear science*, vol. 47, no. 3, pp. 977-81, June 2000.

S. Vandenberghe, et al, "Iterative reconstruction algorithms in nuclear medicine," *Computerized medical imaging and graphics*, vol. 25, pp. 105-11, 2001.

D. Prell, et al, "A novel forward projection-based metal artifact reduction method for flat-detector computed tomography," *Phys Med Biol*, vol. 54, pp. 6575-6591, November 2009

BACKGROUND OF THE INVENTION

A computed tomography (CT) scanner uses X-rays to determine the three-dimensional structure of an object. X-ray beams ("rays") are passed through the object from different angles, and "detector elements" (also known as "detectors") on the other side measure the intensity of each attenuated ray. "Ray" can also refer to the path traversed by X-rays between the source and a single detector, the detector measurement, or to the ray sum (defined below). All of the detector measurements for a single fixed X-ray source and detector configuration are referred to as a "projection." "Projection data" refers to the complete set, or a subset, of detector measurements. Detector measurements can also be expressed as "ray sums," which provide information on the sum of the X-ray attenuation coefficients along each ray. "Ray sums" can also be obtained using other imaging modalities, such as positron emission tomography (PET), or single photon emission computed tomography (SPECT). For these other imaging modalities, "ray sum" refers to the sum of the emitter densities along a given path. The ray sums are then reconstructed into a three dimensional model ("CT image" or "reconstructed image") of the object using a method such as filtered backprojection (FBP), an algebraic reconstruction algorithm such as the algebraic reconstruction technique (ART), or Fourier reconstruction. For CT images, "density" refers to the X-ray attenuation coefficient, which can also be expressed in Hounsfield units. For PET or SPECT images, "density" refers to the emitter density. The reconstructed image consists of a set of density elements, typically called pixels or voxels, which can be arranged in a regular or irregular grid in two or three dimensions.

Given exact projection data with infinite resolution, these methods can reconstruct the object perfectly. However, given noisy data with limited resolution or missing or corrupted data values, the reconstructed image can contain incorrect elements ("artifacts") such as streaking or starburst patterns 10 (as shown in FIG. 3). This is particularly true around high density materials such as bone, metal, metal salts (such as barium sulfate), or iodinated contrast. These artifacts are typically caused by photon counting error (Poisson error), beam hardening effects, edge effects, patient motion, scatter, and other effects. The artifacts can obscure important information, possibly resulting in an incorrect or incomplete diagnosis.

Several strategies have been proposed to reduce artifacts in CT images. Photon counting noise can be reduced by increasing the tube current, which increases radiation exposure to the patient. A beam hardening correction can be applied as a pre-processing step, or as an iterative correction based on the current reconstructed image. The ART method can be modified to converge to a maximum likelihood (ML), maximum entropy, or minimum norm solution. Noisy projection data can be replaced with smoothed or interpolated data. Specifically, the linear interpolation (LI) technique erases the metal by replacing rays that pass through metal with values linearly interpolated from rays that pass adjacent to the metal, then uses FBP to reconstruct the image. (B. De Man, et al, "Reduction of metal streak artifacts in x-ray computed tomography using a transmission maximum a posteriori algorithm," *IEEE transactions on nuclear science*, vol. 47, no. 3, pp. 977-81, June 2000; S. Vandenberghe, et al, "Iterative reconstruction algorithms in nuclear medicine," *Computerized medical imaging and graphics*, vol. 25, pp. 105-11, 2001; D. Verhoeven, "Limited-data computed tomography algorithms for the physical sciences," *Applied optics*, vol. 32, no. 20, pp. 3736-54, Jul. 10, 1993; G. Glover, et al, "An algorithm for the reduction of metal clip artifacts in CT reconstructions," *Medical Physics*, vol. 8, pp. 799-807, November-December 1981; W. Kalender, et al, "Reduction of CT artifacts caused by metallic implants," *Radiology*, vol. 164, pp. 576-77, August 1987.)

Some artifacts still remain after using these existing methods. For example, the maximum likelihood method tries to find an image that has the highest probability of generating the projection data, assuming that photon counts in each detector element follow a Poisson distribution. This ignores other sources of error, such as scatter, edge effects, or errors in the beam hardening correction. Furthermore, there are many images consistent with the projection data within experimental error, and the maximum likelihood method does not specify which image to pick. Thus, the final reconstructed image depends on the initial image, and how many maximum likelihood iterations are applied. Applying too many iterations results in overfitting and a noisier image. The linear interpolation method effectively erases the metal, and thus reduces streaking due to beam hardening and edge effects. However, it does not address Poisson errors for rays passing through soft tissue and bone. Furthermore, the linear interpolation process can introduce new artifacts (for example, streaks between metal and bone).

Here, we present a method for CT artifact reduction that addresses these issues. This method is called the metal deletion technique (MDT). Reducing artifacts results in clearer resolution images, less radiation use, and more accurate diagnosis.

SUMMARY OF THE INVENTION

The basic concept behind the present invention (MDT) is to use forward projection iteratively to replace detector measurements that involve metal (FIG. 1)

In a preferred embodiment of the invention, an adaptive filter is first applied to the experimental projection data 1 that expands the size of each detector element until at least 30 photons are detected. Next, the initial image is constructed using a combination of metal pixels from FBP 2, and non-metal pixels from LI 3. Finally, metal pixels are erased, and filtered backprojection 7 is iterated four times. On each iteration, rays that pass through metal are replaced 6 with forward projected values 5 from the previous iteration. The end result is to create a self consistent set of projection data with the metal removed.

Several key variations on the basic framework described above can improve the image quality. First, to reduce noise and streaking, an edge-preserving blur filter 4 is applied to the image before forward projection. Second, the forward projected values don't match the original projection data exactly, due to beam hardening, density outside the reconstructed region, and other factors. Therefore, we add a linear function to the forward projected values to eliminate discontinuities when they are spliced back into the experimental projection data. Finally, to further reduce streaking, rays passing near metal are replaced with a weighted average of the experimental projection data and the forward projected data, which allows for a smoother transition.

Previous techniques have used forward projection to reduce metal artifacts in computed tomography. The forward projection metal artifact reduction (FP-MAR) technique segments the image into air, soft tissue, and bone (tissue class segmentation), and then uses forward projection to replace metal data (D. Prell, et al, "A novel forward projection-based metal artifact reduction method for flat-detector computed tomography," *Phys Med Biol*, vol. 54, pp. 6575-6591, November 2009; L. Spies, et al, "Image-wide artifacts reduction caused by high attenuating objects in CT deploying voxel tissue class," U.S. Pat. No. 7,636,461 B2, December 2009). This technique assumes that all soft tissue (for example) has the same Hounsfield units. Furthermore, a dark streak through soft tissue may cause it to be incorrectly classified as air (which would introduce new artifacts).

The present invention solves these problems with FP-MAR as follows. First, instead of tissue class segmentation, an edge-preserving blur filter is used to reduce noise and beam hardening artifacts before forward projection. This allows for use of the actual Hounsfield units, instead of idealized tissue classes. In addition, the edge-preserving blur filter blurs out streaks through soft tissue, thus eliminating the risk of misclassification. The edge-preserving blur filter incorporates information from neighboring pixels, whereas tissue class segmentation only considers one pixel at a time. Second, we iterate the method to improve the results. Third, we apply an adaptive filter to the experimental projection data to reduce photon counting (Poisson) noise.

This invention addresses the major sources of artifacts in CT images. Poisson counting error is reduced by expanding the detector elements in regions with low photon counts. Beam hardening effects, edge effects, and patient motion are addressed by deleting the metal. Projection data that involves metal is then replaced with values derived from the rest of the projection data.

Despite a long history of attempts to reduce metal artifacts in CT, this invention is the first metal artifact reduction technique shown to produce statistically significantly better image quality 8 then other methods for clinical scans (FIG. 3). It avoids introducing new artifacts, which are seen with other methods, such as LI 9 or SART 11. It is also the first metal artifact reduction technique that has been shown to change the imaging diagnosis (FIG. 4).

BRIEF DESCRIPTION OF THE DRAWINGS

FIG. 4 shows CT images from a patient with a history of rectal cancer, who was thought to be cancer free.

DETAILED DESCRIPTION OF THE INVENTION

Figure 1:
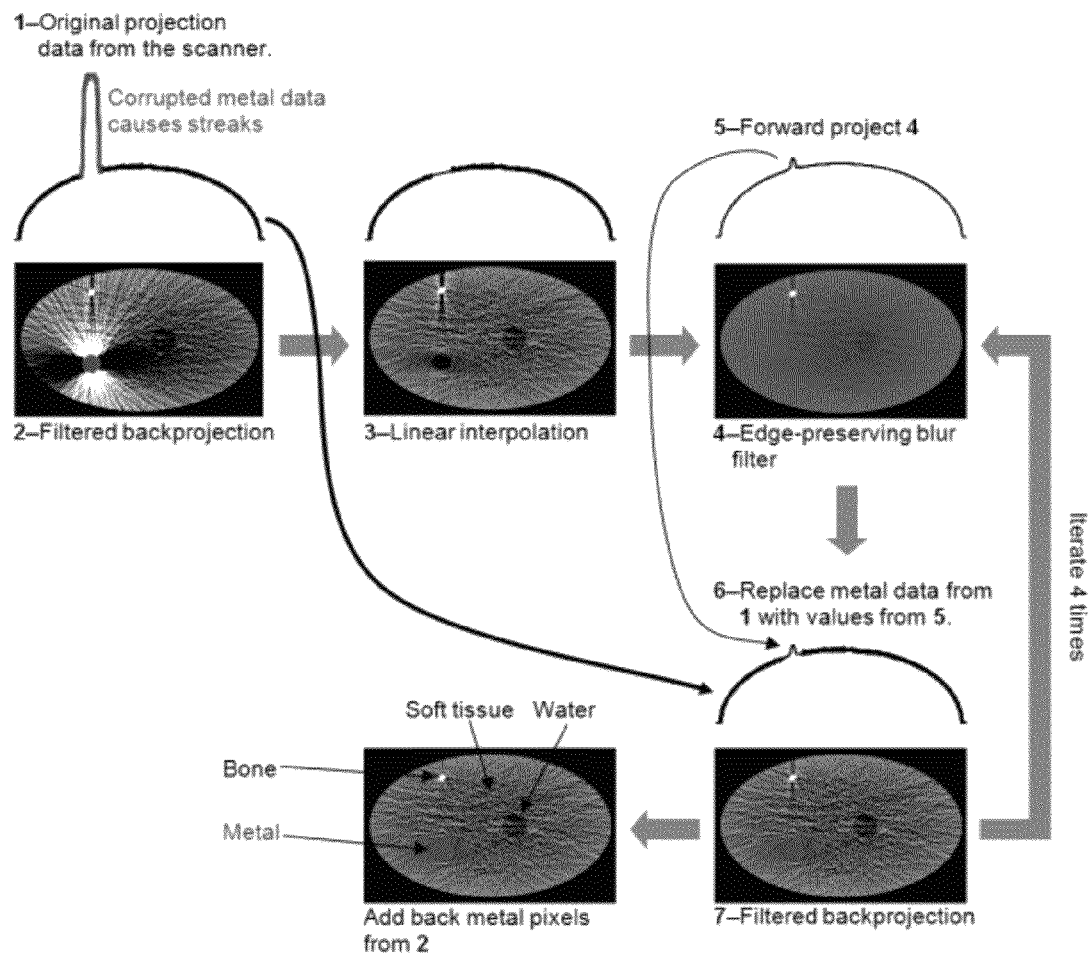
FIG. 1 is a simplified schematic diagram of the present invention (MDT). Forward projection is used iteratively to replace corrupted metal data (which is the cause of the streaks). The end result is that non-metal pixels are solved using only non-metal projection data. Metal pixels and projection data are shown in red. For simplicity, only a single projection is shown. The original projection data are plotted with a thick line, and revised projection data are plotted with a thin line.
Figure 2:
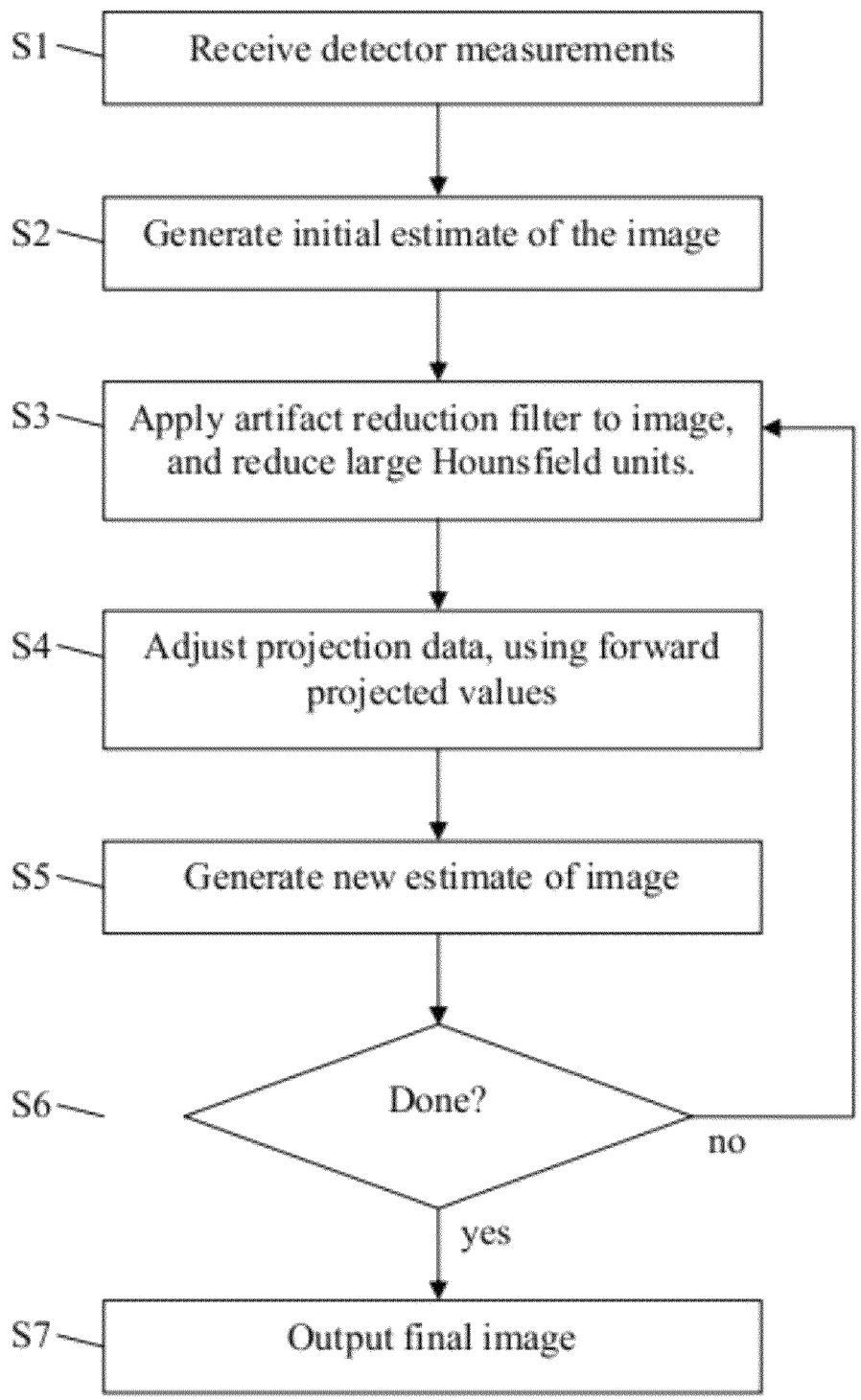
FIG. 2 is a flowchart showing the steps performed in one variation.
Figure 3:
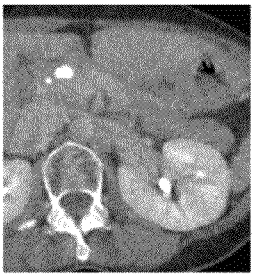
FIG. 3 shows CT images generated using filtered back projection (FBP), linear interpolation (LI), selective algebraic reconstruction technique (SART; US patent application 2008/0273651), and the present invention—the metal deletion technique (MDT). In a blinded comparison of 11 clinical scans, MDT was judged to have the best image quality 100% of the time. The image quality rank shown in the figure ranges from 1 (least streak artifact) to 4 (most streak artifact). MDT has statistically significantly better image quality than LI , FBP, and SART (p=0.0005). Notice the streaks between metal and other high density structures (such as bone or contrast), which are seen in LI and SART, but not MDT.
Figure 3:
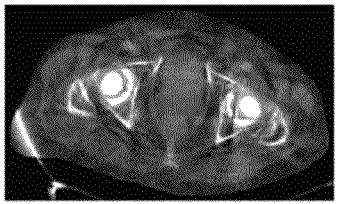
Figure 3:
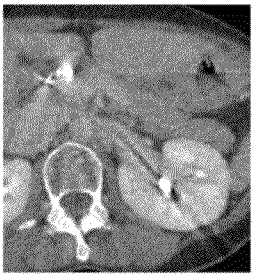
Figure 3:
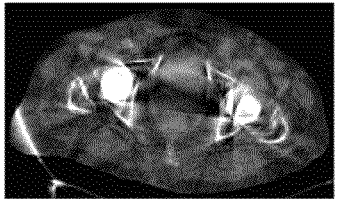
Figure 3:
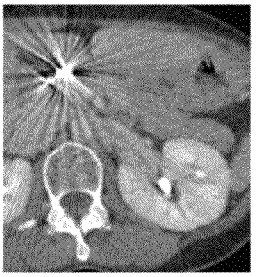
Figure 3:
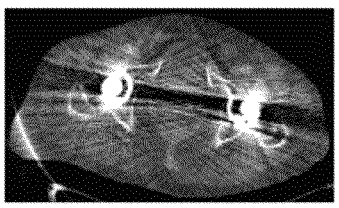
Figure 3:
Figure 3:
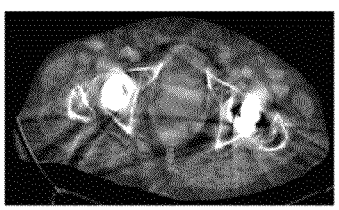
Figures 4A, 4B:
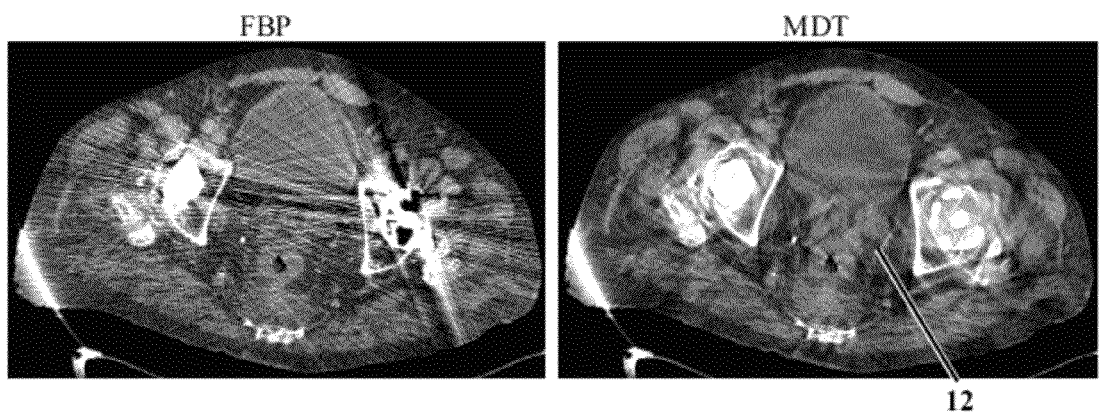
FIG. 4A is an FBP image, which does not show any definite evidence of rectal cancer.
FIG. 4B is the corresponding MDT image, which reveals enlarged lymph nodes 12 around the rectum, suggesting recurrent rectal cancer. These lymph nodes were previously obscured by artifacts from the bilateral hip replacements. Recurrent rectal cancer was found at autopsy.

A flowchart showing one embodiment is illustrated in FIG. 2 and described in detail below.

Step S1. Projection data are obtained from a plurality of detectors configured to detect transmitted, emitted, or reflected photons, other particles, or other types of radiated energy. These measurements are made by a CT, PET, SPECT, or other type of scanner. If the detector measurements are not available (for example, if the manufacturer of the scanner does not allow access to the detector measurements), then experimental projection data can be estimated by forward projecting reconstructed images produced by the scanner. The streaks largely cancel out during the forward projection procedure, thus resulting in a reasonably accurate estimate of the experimental projection data.

Step S2. Generate an initial estimate of the image.

The projection data can be pre-processed to account for beam-hardening, scatter, refraction, diffraction, or other phenomena. Furthermore, low photon counts from nearby rays can be averaged together to reduce the error. The projection data can be interpolated to generate a higher resolution data set. The projection data can be filtered to account for crosstalk between the detectors, or to reduce noise. Many other pre-processing techniques are known to those in the art.

In a preferred embodiment, the detector elements are adaptively expanded in regions with low photon counts. Specifically, rays with fewer than n photons detected can be expanded by adding in adjacent rays (up to m on either side; fractional rays are allowed) until n photons are included. The center ray is then replaced with the average number of photons per ray. A typical value for n would be 30 (range: 5 to 100), and a typical value for m would be 2 (range: 1 to 10). Detector elements from other detector rows could also be included. In that case, nearby detector elements may be specified using a Euclidian or other distance metric, or may be specified in a look-up table or other function.

The initial estimate of the CT image is then generated by an existing CT reconstruction method, such as filtered backprojection. Typically, the image will be represented as a regular array of density elements, such as pixels or voxels. The reconstruction region may be bounded by a circle (cylinder), square (cuboid), or polygon (prism). Of note, reconstructions performed in a square (cuboid) may result in artifacts originating in the corners. These can be reduced by setting pixels near the corners to zero, or by using a circular (cylindrical) reconstruction region. If the experimental projection data was estimated by forward projecting an image reconstructed by the scanner, then this image can be used as the initial estimate.

In a preferred embodiment, an initial FBP calculation is used to detect metal pixels, using a Hounsfield unit cutoff of 3000 (typical range: 1000 to 10,000). A blurring or noise reduction filter may be used before applying the cutoff. In addition, morphological image processing operators, such as erosion or dilation, may be applied to the set of metal pixels. Throughout this document, "metal" is used as a shorthand for any material with large Hounsfield units. Depending on the cutoff used, this could include metal, bone, metal salts (such as barium sulfate), or iodinated contrast (such as iohexol). On the other hand, some metals, such as titanium and aluminum, result in less streak artifact than iron, due to their lower atomic number. In some cases, these metals might be excluded from the selection of "metal" pixels, by adjusting the Hounsfield unit cutoff, manually excluding them, detecting the severity of artifacts around the implant, or some other procedure.

Instead of using a Hounsfield unit cutoff to determine "metal" pixels, an alternative is to use a photon cutoff. If more than a cutoff number of rays passing through a given pixel have below a cutoff photon count, then that pixel is selected. Metal pixels are typically selected based on the initial estimate of the image, and the selection is typically not modified on later iterations.

Rays passing through metal are replaced with log photon counts that are linearly interpolated from rays immediately adjacent to metal. FBP is then performed a second time (resulting in the linear interpolation, or LI, solution). Metal pixels are taken from the initial FBP calculation, pixels more than 10 pixels away from metal are taken from the second FBP calculation (LI), and in-between pixels are a weighted average of the two images, where the weight is a linear function of the number of pixels away from metal.

Artifact reduction steps (steps S2-S5) could be performed on all slices (two dimensional cross sections) of the image, or only on slices that contain significant artifacts.

Step S3. The current reconstructed image is optionally modified to reduce artifacts, and to reduce large Hounsfield units.

Metal pixels are selected using a Hounsfield unit cutoff value of 3000 (typical range: 1000 to 10,000), or a photon cutoff (as described above). The cutoffs could be applied to the initial image, subsequent images, or a combination. The cutoffs may be changed in each iteration. Selected pixels are replaced with different values, typically less than or equal to the metal cutoff. For example, they could all be replaced with the cutoff value, or a different value. Alternatively, various interpolation, boundary value, or other techniques can be used to replace the metal pixels based on the values of the surrounding non-metal pixels. The goal is to reduce any large Hounsfield units or discontinuities that could cause artifacts. In subsequent iterations, after large Hounsfield units have already been decreased, this step can be repeated to ensure that discontinuities or large Hounsfield units do not recur in the former metal pixels. The procedure described in this paragraph is optional.

Either before or after reducing large Hounsfield units, a filter can be applied to the image to reduce noise and artifacts, while attempting to preserve legitimate image details. This filter could be applied either to a two dimensional slice, or to the entire reconstructed three dimensional image. In a preferred embodiment, an edge-preserving blur filter is used. This is a nonlinear filter that smoothes out noise and artifacts, while preserving legitimate edges or other legitimate features. One common edge-preserving filter is a bilateral filter, which operates by replacing each pixel or voxel with a weighted average of neighboring pixels or voxels, where the weights are determined by the distances and the densities of neighboring elements. Specifically, each pixel or voxel in the new image could be calculated as the arithmetic average of nearby pixels or voxels inside a circular region centered on the corresponding element in the current image. To preserve edges, pixels or voxels with densities very different from the center pixel or voxel are excluded from the average, or are downweighted. Selected metal pixels may be excluded from the average. A typical value for the radius of the circular region is 5 cm (typical range: 0.1 to 10 cm). A typical value for the difference in densities that are still included in the average is 400 Hounsfield units (typical range: 40 to 2000 Hounsfield units), or 10% (typical range: 1 to 50%) of the density range of the entire image. These values can be changed on each iteration. For example, the blurring radius can be changed based on the amount of artifact or noise remaining in the image. Furthermore, the blurring radius can be adaptively changed for different parts of the image, depending on local noise characteristics.

Alternatively, edges could be detected using an edge detection method, and the edge information could be incorporated into the filter. For example, the filter could be applied separately to each region bounded by the edges. Alternatively, when selecting nearby pixels or voxels, pixels or voxels on opposite sides on an edge could be excluded. An initial blurring or noise reduction step may improve the performance of the edge-preserving blur filter. Applying two or more noise or artifact reduction filters sequentially is also possible.

Constraints may be applied to the image before or after the artifact reduction step. For example, negative X-ray attenuation coefficients, which are due to noise, can be set to zero.

It is important to note that the final image will not be blurred, and will match the non-metal projection data. However, any local variations in density that are not supported by the non-metal projection data are blurred out.

Many alternative noise and artifact reduction filters are possible. For example, instead of an arithmetic average, one could use a weighted average, median, mode, trimmed mean, or other function. A similar result could be obtained using a low-pass filter, Fourier-transform-based filter, convolution, Fourier-transform-based convolution, non-linear Gaussian filter chain, Kuwahara filter, noise-reduction filter, another edge-preserving blur filter, or another artifact or noise reduction filter. Many other variations will be apparent to those skilled in the art.

Step S4. The current image is forward projected, and a new set of projection data is created by combining the experimental projection data and forward-projected data.

Simulated projection data are calculated for the current CT image (this procedure is called "forward projection"). Each simulated ray sum is calculated as a weighted sum of the pixels or voxels along that ray.

In a preferred embodiment, the projection data is updated using the forward projected data as follows. Rays that go through metal (which were identified on the original image) are replaced with the forward projected values. Rays that do not pass near metal are kept at the experimental values. Rays that pass within r rays of metal are replaced with a weighted average of the experimental and the forward projected values, where the weight linearly ramps between 100% forward projected value (for a ray passing through metal) to 100% experimental value (r+1 rays away from metal). A typical value for r is 3 (typical range: 0 to 10). Importantly, the forward projected values are first adjusted by adding or multiplying a linear, polynomial, or other function so that the adjacent non-metal rays match the experimental projection data. This eliminates discontinuities when the forward projection data is spliced into the experimental projection data. In addition, the adjustment may optionally make first or higher order derivatives match near the junction between metal and non-metal rays.

Many variations of this will be apparent to those skilled in the art. For example, rays with low photon counts or large errors can also be replaced with forward projected values, and nearby rays can be replaced with a weighted average of the forward projected and experimental values. Alternatively, the weights could be based on the expected variances of the experimental and forward projected data. The variance of the experimental data can be calculated from the Poisson distribution. The variance of the forward projected data can be calculated as follows. An error estimate for each pixel or voxel could be based on the local variance in density. This could be forward projected to determine the variance of the forward projected data. Alternatively, the variance of the forward projected data could be calculated from the ray sums, and possibly the ray sums of nearby rays.

Based on the calculated variance, the forward projected data can be adaptively smoothed to reduce noise prior to updating the projection data. Negative forward projected data can be set to zero. Convergence of the forward projected data over multiple iterations can be sped using overrelaxation (also known as series acceleration). Typically, this involves updating forward projection data by extrapolating from previous iterations. Alternatively, any oscillations in the forward projected data over multiple iterations can be reduced using underrelaxation. Typically, this involves interpolating between the new and old forward projected data.

Step S5. Using the new projection data, a new estimate of the image can be generated using FBP or another image reconstruction method.

Step S6. The procedure can be iterated by continuing at Step S3, for a given number of iterations (typically between 1 and 20, with 4 being most preferred), or until termination criteria are met. For example, the procedure could be terminated when the maximum change in density, or the average change in density, or the root-mean-square change in density during the previous iteration falls below a given threshold.

In this step, the projection data can be corrected for beam hardening, scatter, refraction, diffraction, or other effects, using the current CT image. Many methods for doing this are known to those in the art.

Step S7. Pixels with large Hounsfield units that were reduced in step S3 are set back to their original values. The final image is then outputted. The final image may be used for diagnosis, radiation therapy planning purposes, PET/CT attenuation correction, 3D reconstruction, and many other applications.

This invention may be implemented in software on a general purpose central processing unit (CPU), or it may be implemented in specialized hardware, such as an Application Specific Integrated Circuit (ASIC), Field Programmable Gate Array (FPGA), or Graphics Processing Unit (GPU). The calculations may be performed by the scanner itself, or it may be performed by a separate device. The calculations could also be performed using a computing facility where the computer resources (CPU, GPU, memory, storage, network, etc.) can be automatically and rapidly scaled up or down to meet demand (also known as cloud computing).

Specific embodiments of this invention have been described in detail for purposes of clarity. However, it should be understood that the invention is not intended to be limited to the particular forms disclosed. Rather, the invention covers all modifications, equivalents, and alternatives falling within the spirit and scope of the invention as defined by the following claims.

I claim:

1. A method for reducing artifacts in an image, given a set of experimental projection data, wherein the following series of steps is performed one or more times:
    an edge-preserving blur filter step, in which a filter is applied to the current image such that artifacts or noise are reduced while preserving edges, wherein said filter calculates the new density of a pixel or voxel using information about nearby pixels or voxels; followed by
    a forward projection step, in which forward projection data are calculated from the filtered image from the previous step; followed by
    an updating step, wherein a new set of projection data is calculated as a function of the experimental projection data and the forward projection data, and this new set of projection data is used to reconstruct a new image.

2. The method of claim 1, wherein the edge-preserving blur filter step, forward projection step, and updating step are performed two or more times.

3. The method of claim 1, wherein said edge-preserving blur filter step comprises a bilateral filter, a non-linear Gaussian filter chain, a Kuwahara filter, a despeckling filter, a noise-reducing filter, a Fourier-transform-based filter, a convolution-based filter, or a nonlinear filter; or said edge-preserving blur filter step entails calculating each pixel or voxel in the new image as a weighted average, a median, a mode, a trimmed mean, or some other function of nearby pixels or voxels in the current image; and said nearby pixels or voxels (or weights for a weighted average) may be specified using a Euclidian or other distance metric, or may be specified in a lookup table or other function; and said nearby pixel or voxels (or weights for a weighted average) may be further specified based on their density, the density of elements near them, or the density of elements near the element being calculated.

4. The method of claim 1, wherein the new projection data is a weighted average of the forward projected data and the experimental projection data, where the weight for each ray is a function of the photon count of the ray and nearby rays, and the density of pixels or voxels along the ray and nearby rays in the current image or previous iterations of the image; wherein said nearby rays may be specified using a Euclidian or other distance metric, or may be specified in a look-up table or other function.

5. The method of claim 1, wherein the forward projected data are adjusted to reduce or eliminate discontinuities when they are combined with the experimental projection data.

6. The method of claim 1, wherein the experimental projection data are estimated by forward projection of the initial image.

7. The method of claim 1, wherein there is at least one step where pixels or voxels with density above a cutoff value in the current image or previous iterations of the image, are set to a value less than or equal to the cutoff value.

8. The method of claim 1, wherein the projection data are pre-processed by expanding detector elements in regions with low photon counts; wherein fractional detector element sizes and overlapping detector elements are allowed.

9. A computed tomography system comprising:
a plurality of detectors configured to detect transmitted, emitted, or reflected photons, other particles, or other types of radiated energy; and
a processor configured to calculate an image from the detector signals, wherein the processor calculates an initial image consistent with a set of projection data, then updates the image by performing the following series of steps one or more times: an artifact reduction step, in which an edge-preserving blur filter is applied to the current image, followed by a forward projection step, in which forward projection data are calculated from the filtered image from the previous step, followed by an updating step, wherein a new set of projection data is calculated as a function of the experimental projection data and the forward projection data, and this new set of projection data is used to reconstruct a new image.

* * * * *